(12) United States Patent
Vigh et al.

(10) Patent No.: US 11,508,070 B2
(45) Date of Patent: Nov. 22, 2022

(54) METHOD AND APPARATUS TO CLASSIFY STRUCTURES IN AN IMAGE

(71) Applicant: Medtronic Navigation, Inc., Louisville, CO (US)

(72) Inventors: Rowena Vigh, Superior, CO (US); Hallehsadat Ghaderi, Superior, CO (US); Daniel H. Adler, Broomfield, CO (US); Shai Ronen, Louisville, CO (US); Nikhil Mahendra, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 254 days.

(21) Appl. No.: 16/862,890

(22) Filed: Apr. 30, 2020

(65) Prior Publication Data

US 2021/0343018 A1    Nov. 4, 2021

(51) Int. Cl.
| | |
|---|---|
| *A61B 34/20* | (2016.01) |
| *G06T 7/90* | (2017.01) |
| *A61B 5/055* | (2006.01) |
| *G06T 7/11* | (2017.01) |
| *G06T 7/50* | (2017.01) |
| *A61B 5/00* | (2006.01) |
| *A61N 1/05* | (2006.01) |
| *G06K 9/62* | (2022.01) |
| *G06T 7/60* | (2017.01) |

(52) U.S. Cl.
CPC .............. *G06T 7/11* (2017.01); *A61B 5/0042* (2013.01); *A61B 5/055* (2013.01); *A61B 34/20* (2016.02); *A61N 1/0534* (2013.01); *G06K 9/628* (2013.01); *G06K 9/6256* (2013.01); *G06T 7/50* (2017.01); *G06T 7/60* (2013.01); *G06T 7/90* (2017.01); *A61B 2034/2051* (2016.02); *A61B 2034/2065* (2016.02); *G06T 2207/10088* (2013.01); *G06T 2207/20081* (2013.01); *G06T 2207/20084* (2013.01); *G06T 2207/30016* (2013.01); *G06T 2207/30052* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 9,311,335 B2 | 4/2016 | Simon | |
| 11,152,123 B1 * | 10/2021 | Sughrue | ............... A61B 5/4848 |
| 2009/0232374 A1 | 9/2009 | Simon | |

(Continued)

FOREIGN PATENT DOCUMENTS

| | | |
|---|---|---|
| WO | 2016040260 A1 | 3/2016 |
| WO | 2019157174 A1 | 8/2019 |

OTHER PUBLICATIONS

U.S. Appl. No. 16/862,840, filed Apr. 30, 2020, Vigh, et al.

(Continued)

*Primary Examiner* — Idowu O Osifade
(74) *Attorney, Agent, or Firm* — Harness, Dickey & Pierce, P.L.C.

(57) ABSTRACT

Disclosed is a system and method for segmentation of selected data. In various embodiments, automatic segmentation of fiber tracts in an image data may be performed. The automatic segmentation may allow for identification of specific fiber tracts in an image.

20 Claims, 7 Drawing Sheets

(56) References Cited

U.S. PATENT DOCUMENTS

| | | | |
|---|---|---|---|
| 2011/0199084 A1* | 8/2011 | Hasan | G06T 1/00 |
| | | | 324/309 |
| 2012/0226138 A1* | 9/2012 | DeSalles | A61B 5/4893 |
| | | | 600/410 |
| 2013/0009959 A1 | 1/2013 | Calamante et al. | |
| 2014/0012131 A1* | 1/2014 | Heruth | A61B 34/20 |
| | | | 607/62 |
| 2017/0052241 A1 | 2/2017 | Cetingul et al. | |
| 2018/0018790 A1* | 1/2018 | Lachner | G06T 7/251 |
| 2019/0082990 A1 | 3/2019 | Poltorak | |
| 2019/0247662 A1 | 8/2019 | Poltroak | |
| 2019/0331751 A1* | 10/2019 | Zuccolotto | G01R 33/31 |
| 2020/0383730 A1* | 12/2020 | Hodges | G16H 40/20 |
| 2021/0118226 A1* | 4/2021 | Sughrue | G06T 17/20 |
| 2021/0338172 A1 | 11/2021 | Vigh et al. | |
| 2021/0343018 A1 | 11/2021 | Vigh et al. | |

OTHER PUBLICATIONS

U.S. Appl. No. 16/862,882, filed Apr. 30, 2020, Vigh, et al.

International Search Report and Written Opinion regarding International Application No. PCT/US2021/029812, dated Aug. 12, 2021.

International Search Report and Written Opinion regarding International Application No. PCT/US2021/029798, dated Aug. 11, 2021.

International Search Report and Written Opinion regarding International Application No. PCT/US2021/029803, dated Aug. 11, 2021.

Dhollander, et al.: Time to move on: an FOD-based DEC map to replace DTI's trademark DEC FA; Proc. Intl. Soc. Mag. Reson. Med. 23 (2015), 2 pages.

Garryfallidis, et al.: Recognition of white matter bundles using local and global streamline-based registration and clustering; NeuroImage, Jul. 2017; DOI: 10.1016/J.neuroimage.2017.07.015; 13 pages.

Liu, et al.: DeepBundle: Fiber Bundle Parcellation with Graph Convolution Neural Networks; arXiv: 1906.03051v1 [eess.IV]; Jun. 7, 2019; 8 pages.

Wasserthal, et al.: TractSeg—Fast and accurate white matter tract segmentation; NeuroImage, vol. 183, Dec. 2018, pp. 239-253; 40 pages.

Zhang, et al.: Identifying White-Matter Fiber Bundles in DTI Data Using an Automated Proximity-Based Fiber Clustering Method; IEEE Trans Vis Comput Graph. Sep. 2008-Oct.; 14(5): 1044-1053; DOI: 10.1109/TVCG.2008.52; Oct. 6, 2009; 21 pages.

Nordin et al., "White matter tracing combined with electric field stimulation—A patient-specific approach for deep brain stimulation," NeuroImage: Clinical 24 (2019) 102026 (Year: 2019).

\* cited by examiner

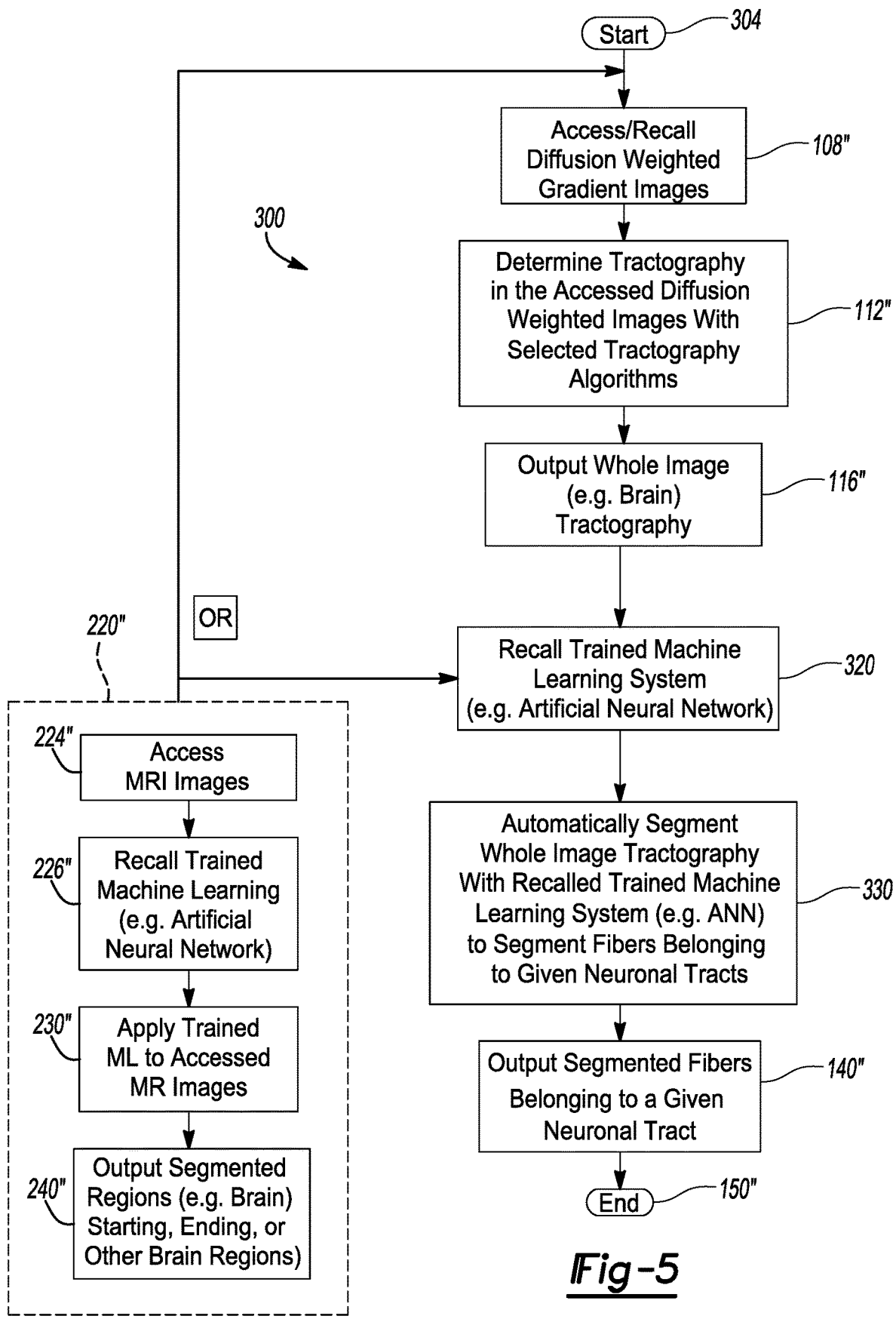

METHOD AND APPARATUS TO CLASSIFY STRUCTURES IN AN IMAGE

CROSS-REFERENCE TO RELATED APPLICATIONS

This application includes subject matter similar to that disclosed in U.S. patent application Ser. No. 16/862,840, filed Apr. 30, 2020 and U.S. patent application Ser. No. 16/862,882, filed Apr. 30, 2020. The entire disclosures of each of the above Applications are incorporated herein by reference.

FIELD

The subject disclosure relates to a tractography, and particularly to a tractography classification method and system.

BACKGROUND

This section provides background information related to the present disclosure which is not necessarily prior art.

An imaging technique may be used to acquire image data of a subject. Image data of a subject can include one or more types of data to visualize one or more structures of the subject. Structures may include external or internal structures of the subject. In various systems, for example, an image may be acquired of an internal structure of a subject with a selective imaging technique.

The image data may be used to generate images that are displayed for viewing by a user. The images may be displayed on a selected system, such as a display device, for a visual inspection by a user. Generally, the user may view the images to assist in performing a procedure on the subject.

SUMMARY

This section provides a general summary of the disclosure, and is not a comprehensive disclosure of its full scope or all of its features.

A method may be used to identify and/or classify various structures in data, such as an image data. The structures may be identified as fibers or tracts, such as in a brain of a subject, such as a human subject. It is understood, however, that the process may be used to identify tracts in any appropriate subject. Generally, the tracts are neuronal tracts that include white matter axons. The method may be used to identify various tracts in a brain to assist in various procedures, such as tumor resection, implant placement (e.g. deep brain stimulation leads), or other appropriate procedures.

In various embodiments, the process may be used to identify neuronal tracts even in the presence of an aberration of standard anatomy. For example, a tumor may grow in a brain, which may affect generally understood or present neuronal tracts. Therefore, the process may assist in identifying neuronal tracts even in the presence of a tumor or other abnormal anatomy in the image data.

The neuronal tracts may then be displayed for various purposes. The tracts may be used to identify various features and/or structures of the brain to assist in a procedure. Further, the images may be used to assist in performing a procedure, such as tumor resection or implant positioning in a selected subject. Accordingly, the image data may be used to identify tracts in the image data and the tracts and/or other appropriate features may be displayed with the display device in one or more images.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is a flow chart of a method of segmenting image data, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
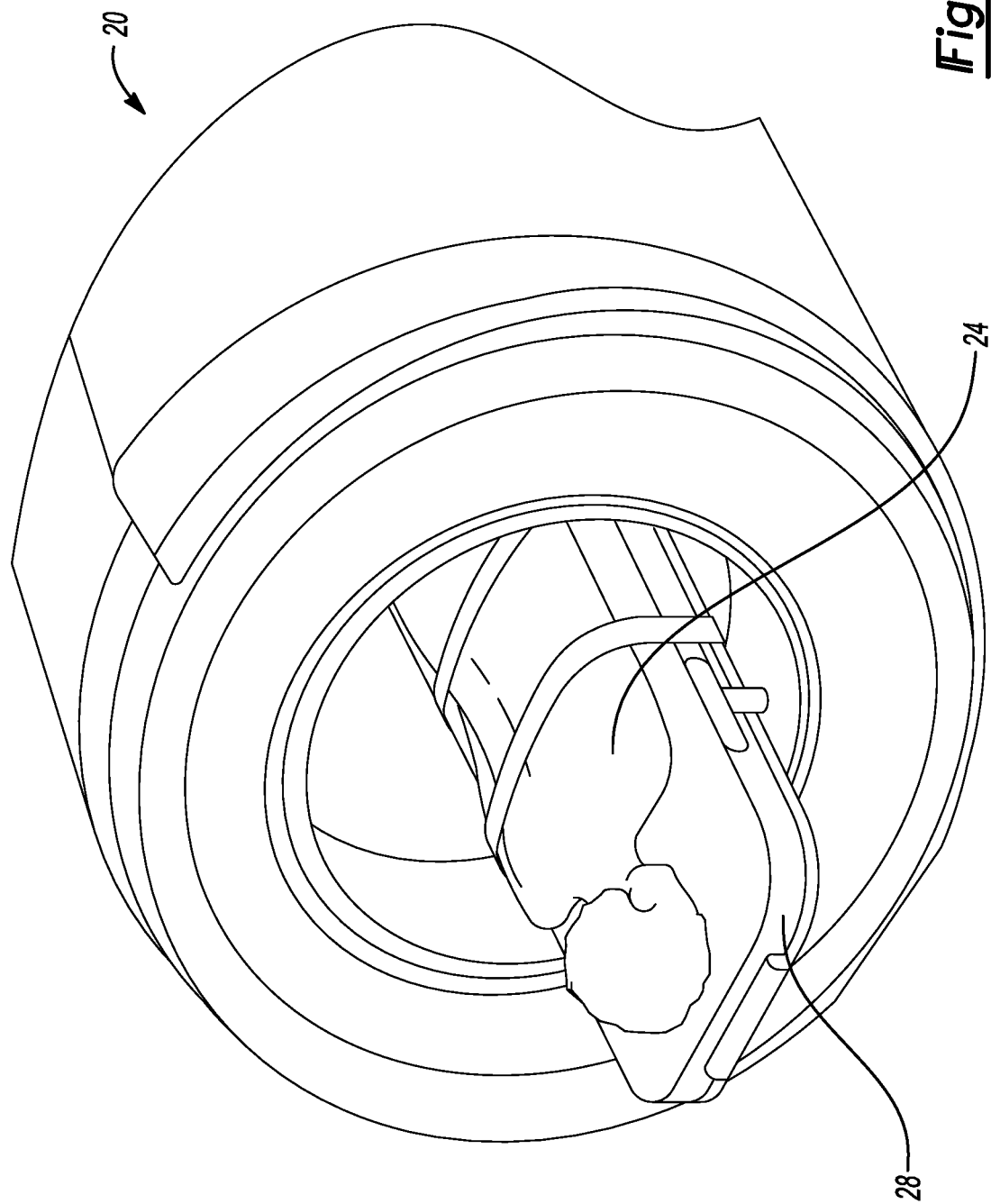
FIG. 1 is an environmental view of an imaging system and subject.

A system may be used to acquire image data of a subject. For example, as schematically illustrated in FIG. 1. Generally, a subject may be imaged with a selected imaging system 20. The imaging system 20 may be any appropriate imaging system to acquire a selected image data of a subject 24, such as a magnetic resonance imager (MRI). The MRI may operate in various manners or modes, such as including a diffusion weighted data acquisition manner. In a diffusion weighted technique, the diffusion or movement of water may be determined or estimated to assist in determining tracts, as discussed further herein. The imaging system 20 may include a selected support 28 to support the subject 24 during movement through the imaging system 20. The imaging system may include components generally known to those skilled in the art. It is understood, however, that any appropriate MRI imaging system may be used as the imaging system 20, or any other appropriate imaging system. Nevertheless, the imaging system 20 may be operated to generate image data of the subject 24.

Figure 2:
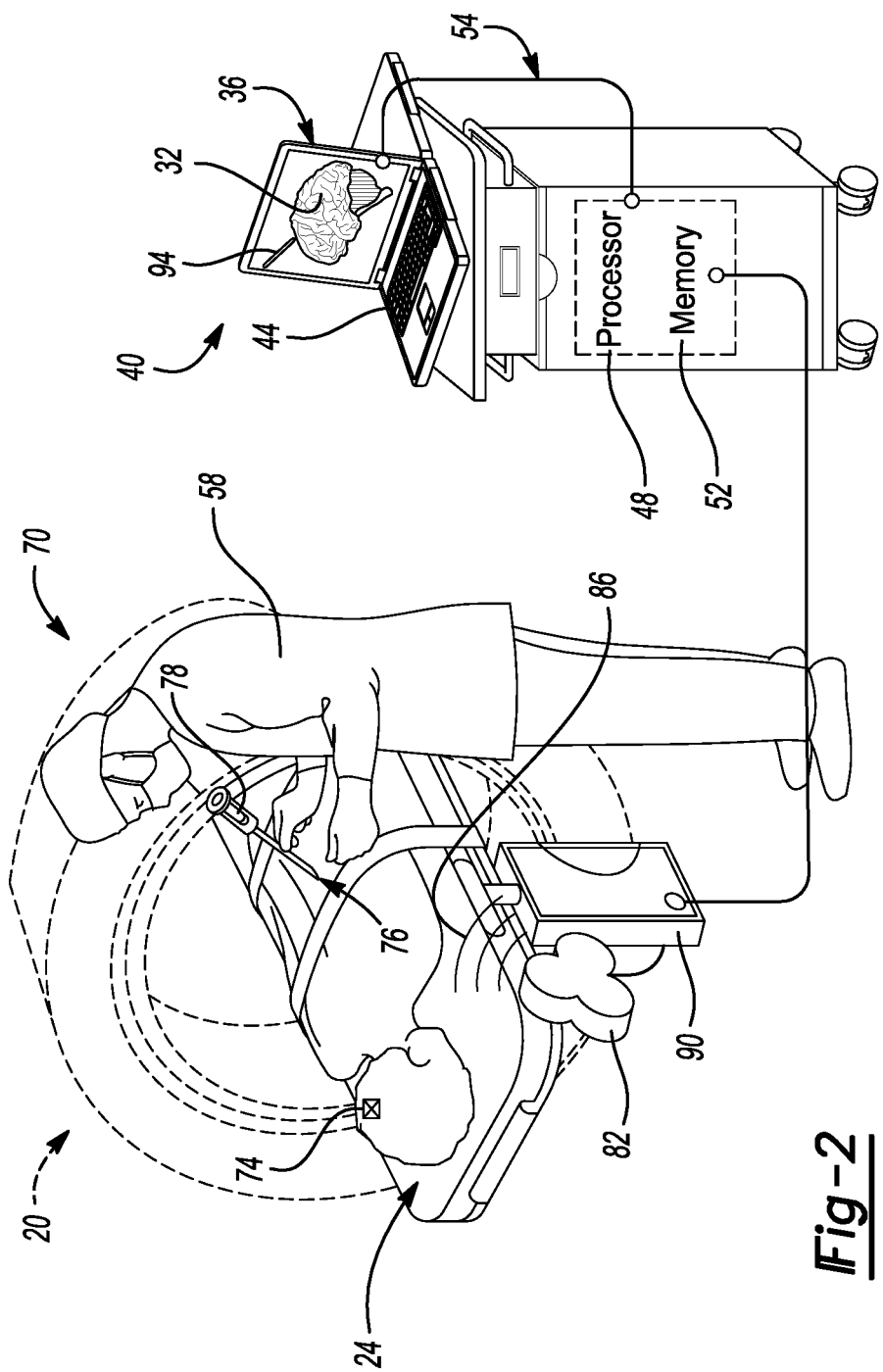
FIG. 2 is an environmental view of a procedure room.

With continuing reference to FIG. 1 and additional reference to FIG. 2, the subject 24, either after acquiring the data, which may include anatomical image data and/or diffusion weighted data, with the imaging system 20 and/or during acquisition (e.g. with an appropriate imaging system) may be moved or positioned into a selected operating theater for performing a procedure. While or to plan for performing a procedure on the subject 24, an image 32 of the subject 24 may be displayed on a display device 36 of a selected workstation or system 40. The display of the image 32 may be used for various reasons, such as preparing for a procedure on the subject 24, assisting in performing a procedure on the subject 24, or other appropriate purposes. As discussed herein, for example, the image 32 may include illustration of tracts identified in the image 32 and/or the image data acquired with the imaging system 24 for display on the display device 36. The tracts may include fiber neuronal tracts in the brain of the subject 24. The tracts may also include other appropriate tracts, such as fiber tracts in a spinal cord. An anatomical or known fiber tract may also be referred to as a given fiber tract.

The workstation or processor system 40 may include various portions or features, such as an input device 44, a processor portion or module 48 and a memory 52. A selected connection, such as a wired or wireless connection 54 may connect the processor 48 and/or the memory 52 with the display device 36 and/or the input device 44. Therefore, a selected user, such as a user 58 may provide input or select input for the system 40 and/or view the display device 36, such as a view of the image 32.

In various embodiments, the image 32 may be registered to the subject 24 for a selected procedure. For example, a tumor resection, implant placement, or the like may be performed on the subject 24. It is understood that the subject 24, however, may be an inanimate object and other appropriate procedures may be performed, such as a part replacement or connection. Imaging and registration may occur in an appropriate manner, such as those disclosed in U.S. Pat. No. 9,311,335, issued Apr. 12, 2016, incorporated herein by reference. Briefly, registration may include a translation between subject space defined relative to the subject 24 and image space defined by the image 32. A coordinate system may be developed for both spaces and a translation map may be made therebetween.

In various embodiments, for registration, portions of the subject 24 may be identified, such as by the user 52, and identical portions may be identified in the image 32. A registration between the subject space and the image space may then be made by generating or determining a translation map between the subject space and the image space based upon the identified similar or identical points, also referred to as fiducial points. The processor module 48 may execute instructions to perform the translation and registration of the subject space to the image space.

After registration a navigation system 70, which may incorporate the workstation or processor system 40, may selectively perform the translation and registration that may be used to assist in performing a procedure. Once registration occurs a dynamic reference frame or patient reference device 74 may be connected or fixed to the subject 24. The DRF 74 may include a tracking device or portion that is tracked with the navigation system 70 to determine movement of the subject 24 and maintain registration with the image 32. An instrument tool 76 may also be tracked with the selected tracking device, such as a tracking device 78 associate with the instrument, such as attached thereto, for a procedure. The instrument may be at least one of a deep brain stimulation lead that may be implanted. In addition to the instrument, selected procedures may also be tracked and/or determined such as computing a volume of activation for a DBS lead and/or computing a thermal ablation estimate for an ablation. In various embodiments, a localizer 82 may generate a field 86 that is sensed by the tracking device 78 and/or DRF 74 to allow for tracking with the navigation system 70. A controller, such as a coil array controller 90 may receive a signal from the localizer 82 and/or control the localizer 82 and/or receive a signal from the tracking device 78 and transmit it to the workstation processor module 48. The processor module 48 may then execute instructions to determine a location of the tracking device 78 relative to the subject 24 to allow for navigation of the instrument 76 relative to the subject 74. Thus, a graphical representation 94 of the tracked portion (e.g. instrument 76) may be displayed on the display device 36 relative to the image 32 to display a real-time position of the instrument 76 relative to the subject 24 by displaying the graphical representation 94 of the instrument relative to the image 32. Generally, the tracking system is able to track and illustrate a position or pose of the tracked portion. The position may include three dimensional location and one or more dimensions orientation. Generally, at least four degrees of freedom information, including at least six degrees of freedom, or any selected amount.

As discussed further herein, the image 32 may include selected image features, such as tracts of the brain, and the graphical representation 94 may be displayed relative thereto. Accordingly, defining or determining tracts for performing a procedure may assist in performing a selected procedure, as discussed further herein.

As discussed above, the imaging system 20 may be used to generate image data of the subject 24 for a selected procedure. The Image data may be processed, according to the processes, including one or more processes, as discussed further herein. The image data, following a selected process or plurality of processes, may be used to generate one or more images for display on the display device 36. Further, the various processes may be used to identify features that may also be output by a selected processing system, such as the processor module 48, as discussed herein.

Disclosed herein, according to various embodiments, are systems and methods to identify, such as by segmentation, image or data portions. For example, one or more fiber bundles or tract may be segmented. A fiber tract may include one or more fibers that are segmented by a system that are intended to represent the neuronal tract in a subject's brain. A fiber or line includes an individual line produced by a selected system (e.g. algorithm) that may be one or a part of a set of lines, intended to represent the physical neuronal tract in a subject's brain. A white matter tract or anatomical tract is a physical bundle of axons in the subject's brain that convey electrical signals from one region of the brain to another and is intended to be represented by a fiber tract. There may be more than one fiber tract and white matter tract in any given data. A given fiber tract or white matter tract may be a predetermined or named tract.

Figure 3:
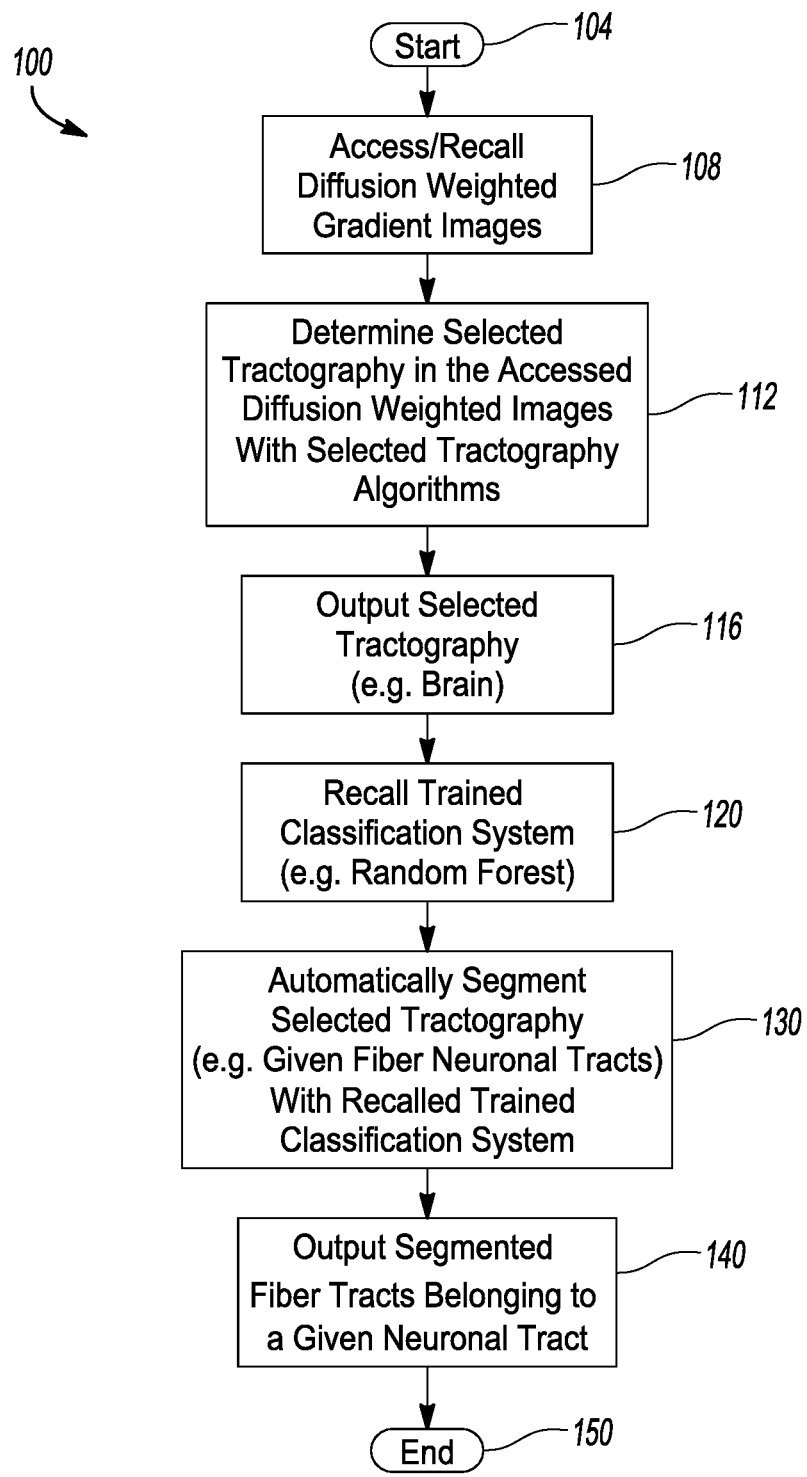
FIG. 3 is a flow chart of a method, according to various embodiments, of segmenting image data.

With initial reference to FIG. 3, and continuing reference to FIGS. 1 and 2, a method of identifying or segmenting fiber tracts or bundles is illustrated in the process 100. The process may be used to identify, such as by segmenting selected fiber tracts, which may also be referred to as given fiber tracts. The fiber tracts may be brain fiber tracts and also referred to as given fiber neuronal tracts. The segmentation may include segmenting (i.e. classifying which fibers belong to a given neuronal tract) the given tracts from other tracts and/or other data, such as image data. It is understood that the segmentation may occur according to various embodiments, including combinations thereof, as discussed herein.

Initially, the process 100 may start in start block 104. Starting in the start block 104 may include appropriate measures or steps, such as assessing a patient, positioning a patient or a subject for imaging, evaluating a subject, or evaluating a possible treatment or diagnosis of a subject. It is understood, however, that in start block 104 any appropriate procedures may occur. After starting the process 100 in start block 104, diffusion weighted gradient images or appropriate data may be accessed or recalled in block 108. It is understood that the process 100 may include acquiring image data, such as with the imaging system 20, in block 108.

In various embodiments, the image data may be acquired at any appropriate time and saved in a selected manner to assist in performing a procedure. Therefore, accessing or recalling the image data in block 108 may include acquiring image data of the subject with an imaging system, such as the imaging system 20, as discussed above and/or recalling previously acquired image data. For example, image data may be acquired at a first instance, such as during an initial diagnosing or testing process and this data may be used in the procedure 100. Accordingly, the image data may be accessed in block 108 rather than acquired and new. Also, or alternatively, image data may be acquired of the subject 24 during or in a procedure location (e.g. operating room for a resection or implantation).

After the image data is accessed in block 108, a determination of a selected tractography may occur in block 112. The determination of the selected tractography in block 112 may include a whole image tractography including identifying all possible fiber lines or tracts given the acquired image data according to one or more various known techniques. Various techniques may include identifying or attempting to identify all possible tracts with or by a selected algorithm and/or user. For example, the tractography may be performed according to appropriate techniques, such as appropriate algorithmic techniques. For example, a tractography may be performed with a diffusion tensor imaging tractography system such as the tractography system included with the StealthViz® tractography and image guided surgery system, sold by Medtronic, Inc. Other appropriate tractography techniques can include that described in U.S. Pat. No. 9,311,335, issued Apr. 12, 2016.

In various embodiments, in addition or alternatively to an entire or whole image tractography (e.g. an entire brain tractography), a selected tractography may be or include less than a whole image tractography. The selected tractography may, therefore, include a subset of a whole image tractography. For example, between only selected regions of interest (e.g. half of a brain, or in a brain stem), etc. Thus, a selected tractography generated for a segmentation/identification process, as discussed herein, may include a whole image tractography and/or only a subset of a whole image tractography. Further, while a whole image tractography may be generated, only a subset of the fiber lines or tracts may be analyzed for segmentation. Accordingly, discussion herein to the image tractography in block 112 or equivalents is understood to include a whole image tractography, a selected image tractography, or combinations thereof unless specifically stated otherwise.

After determining the selected tractography in block 112, the selected tractography may be output in block 116. In various embodiments, the image may include an image of a brain of the subject 24, such as a human subject. Accordingly, the whole image tractography may include tractography of a whole brain. A selected tractography may be a portion thereof, as discussed above. It is understood, however, that the brain or image tractography output in block 116 may include simply or only a determination of possible connection of all tracts. As is understood by one skilled in the art, the tractography may include a determination of a possible or average movement or tendency of movement of a selected material, such as water. Therefore, the tractography output in block 116 may simply be all possible tracts or connections and/or selected tracts identified within the accessed image data 108. Therefore, the tractography output in block 116 may not define or identify, either completely or with accuracy, particular anatomical neuronal tracts within the subject.

The output tractography may then be segmented to output or identify selected or given fiber tracts, such as neuronal tracts (e.g. corticospinal tracts, optical tracts, etc.) by recalling a trained classification system in block 120. The trained classification system may include a random forest classification system that has been trained to use various features, such as fiber points and image features, to classify whether fibers in a selected tractography belong to specific neuronal tracts. The brain tractography, as discussed above, may include any identified tracts or connections of possible or average diffusion of a material, such as water within the image. Accordingly, the segmentation of the image tractography may attempt to identify or classify various possible tracts relating to certain anatomical functions or features, such as the corticospinal tracts (CST), orbital or eye tract, or other appropriate anatomical or neurological tracts.

The classification system may be trained using various parameters that may be learned parameters for different tracts. Parameters of features may include various parameters of features that are identifiable and may be evaluated within the image tractography. Features may include identified points and their locations on the tracts in the image tractography. Line segments between the points and/or vectors from each point. Fractional anisotropy (FA) at each point. Diffusion encoded color (DEC) values at each point. Curvature at each point, such as of the line segment to the next point. A comparison to an atlas of known fiber tracts or known brain regions at the determined points or selected number of points. An atlas may be a generally known atlas of selected fiber tracts (e.g. a brain neuronal tract atlas) or known brain regions. A distance or length of the tracts from respective starting regions to ending regions. Additional or other image properties at each point and/or anatomical gradient magnitudes within the image. These features may be trained with a plurality of data, such as previously classified data. The previously classified data may be classified by a reading expert (e.g. a neurosurgeon).

The trained classification system may then be used to classify tracts within the image tractography 116. For example, instructions may be saved and recalled from the memory 52 including one or more of the features noted above. The image tractography may then be evaluated with the classification system to identify given tracts. The segmented tracts may also be referred to as identified or segmented tracts.

The trained classification system recalled in block 120 is used for segmenting given fiber tracts. Automatic segmentation of the image tractography may then occur in block 130. As discussed above, the system may include a workstation or processor system 40 that may include the processor module 48. The processor module 48 may be in communication with the memory 52. The memory 52 may include the accessed image data 108 and the classification system that may be recalled in block 120.

The processor module 48 executes or evaluates the accessed data from block 108 with the trained classification system to the brain tractography to automatically segment fiber tracts, such as neural tracts or neural fibers, in the image tractography in block 130. Automatic segmentation may occur by applying the classification system to the selected image tractography. The automatic segmentation applies the classification parameters to the selected tractography and, therefore, may generate or determine a selected image segmentation (including a whole or subset segmentation). In various embodiments, the automatic segmentation may identify selected features, such as of a region of interest (ROI) (e.g. possible start and ending regions) or other brain areas that the tract passes or doesn't pass through and use those to classify the fibers. In classifying tracts, the classification system may identify the given fiber tract which may be or is a neuronal tract, i.e. anatomical feature tract. The anatomical feature may be preselected by a user, such as the user 78, or may be identified by a system such that all possible tracts are segmented and identified.

The automatic segmentation in bock 130 may be performed by evaluating the selected image tractography with the processor module 48 by executing the instructions and the recalled classification system. The automatic segmentation therefore may determine or identify segmented fiber tracts may be output in block 140. Outputting the segmented fiber tracts in block 140 may include outputting all fiber tracts that have a selected confidence interval to be identified as a selected tract based upon the classification system recalled in block 120. The output in block 140 may include only those tracts selected to be identified by a user 78, or other appropriate system, and/or may include identification and output of all possible tracts from the classification system 120. Accordingly, the classification system 120 may be trained to identify a plurality of tracts (e.g. CST, optical, auditory, etc.) and all trained tracts may be segmented and output in block 140. Therefore, the output 140 may include all tracts which the system is trained and/or only selected tracts based upon a selection of the user 78 or other appropriate selection.

The method 100 may then end in block 150. Ending in block 150, the selected procedure 100 may allow for further analysis for procedures to occur. As discussed above, the selected segmented (i.e. identified) tracts may be used for selected procedures, such as tumor resection, implant positioning, or other appropriate determinations. Therefore, after or in the ending block 150, the user 78 may identify a specific location or tracts relative or near a tumor for resection of the tumor. Further, the user 78 may identify tracts relative to a tumor or other physiological anomaly that may affect (e.g. move) the tract, in the subject 24, from generally known or identified tracts to assist in positioning an implant in the subject 24, or the like.

In various embodiments, the output segmented fiber tracts in block 140 may be displayed on the display device 36, such as relative to an image of the subject 24 (e.g. a 3D MRI of the subject 24) to assist in a procedure. As discussed above, the image 32 may be registered to the subject 24. Accordingly, the output segmented fiber tracts from block 140 may be superimposed on the image 32 to assist in performing a procedure on the subject 24. The icon or graphical representation 94 of the instrument 76 may, therefore, also be displayed relative to the output segmented fiber tracts from block 140. It is understood that the output segment fiber tracts may also be displayed as a graphical representation superimposed on the image generated from the image data of the subject 24 and displayed as the image 32.

The method 100, therefore, may be used to automatically segment given fiber tracts, such as in a brain of the subject 24. The segmented fiber tracts may be used to assist in a procedure, such as in the end block 150. The procedure may be a navigated procedure to for implantation of a lead (e.g. deep brain stimulation lead), a resection of a tumor, etc. The automatic segmentation may be performed by the processor module 48 by evaluating the image tractography with the recalled classification system.

Figure 4:
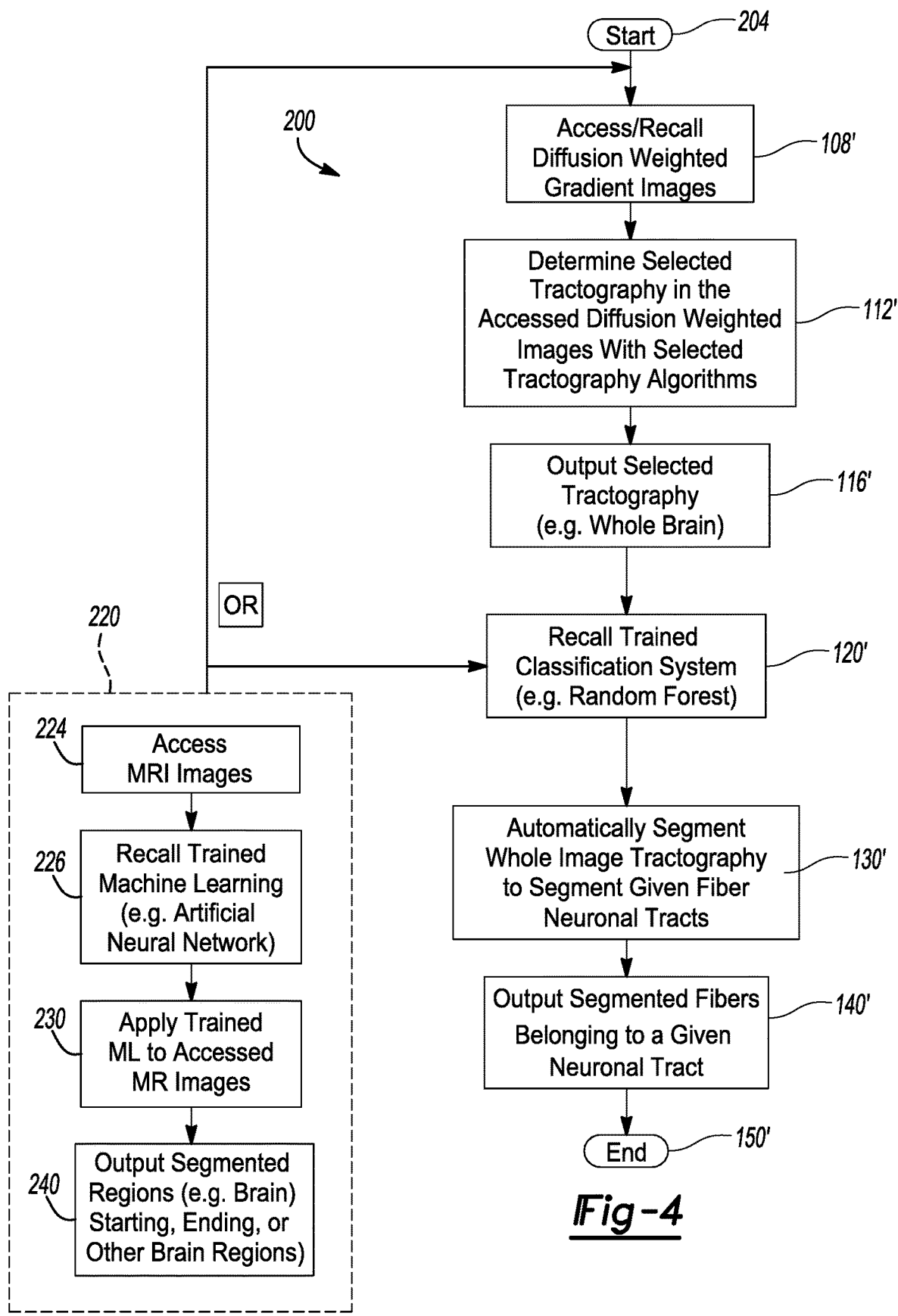
FIG. 4 is a method, according to various embodiments, of segmenting image data.

Turning reference to FIG. 4, and with continuing reference to FIG. 1 and FIG. 2, a process for identifying or segmenting neuronal fiber tracts is illustrated in method 200. The method 200 may include additional features, in addition to those discussed above in relation to the method 100, and/or may include steps or processes similar or identical to those discussed above. Accordingly, similar processes will be included with the similar or same reference numerals, augmented by a prime C) and will not be discussed in detail here. It is understood that the processes so identified may be identical to those discussed above and/or may be similar and include slight noted augmentations related to the specific method illustrated in the process 200.

Initially, the method 200 may begin in start block 204, which is similar to the start block 104, as discussed above. The method 200 may then proceed to access and/or recall diffusion weighted gradient images in block 108'. The accessed or recalled diffusion weighted gradient images may be similar to those discussed above in block 108. The diffusion weight images may then have selected tractographies determined in block 112'. The selected image tractography may be similar to the image tractography in block 112, as discussed above. Further, the image tractography may then be output in block 116'. Again, the output of the selected image tractography may be similar to the image output in block 116, as discussed above.

The process of accessing or recalling diffusion weighted images in block 108', image tractography in block 112', and an output of image tractography in block 116' may be similar to that as discussed above. Therefore, the details thereof will not be repeated here and may be referred to above.

The process 200, however, may further include additional and/or alternative processes, including generating a noisy diffusion tractography based on the selected tractography form block 112'. The noisy tractography may be generated with various additional inputs, as discussed herein. The noisy diffusion tractography, therefore, may include and/or be the result of a selected tractography algorithm that identifies the possible tracts due to the diffusion weight information collected in the image data accessed in block 108'.

The method 200 may also include a second or secondary input path or portion 220. The sub-process, in various embodiments, may be an input with the accessed diffusion weighted gradient images in block 108'. The secondary input may assist in identifying regions of interest (ROIs) within the at least selected portions, including the, image, such as within the brain. The input sub-process 220 may include MR images (which may include FA images) may be accessed in block 224. The MR images accessed in block 224 may be images that are acquired with the diffusion weighted gradient images in block 108'. As is understood by one skilled in the art, the diffusion weighted gradient images may be acquired as a process of acquiring images with an MRI system. Accordingly the MR images may be acquired substantially simultaneously with the diffusion weighted gradient images accessed in block 108'.

The sub-process 220 may further include a machine learning system, such as an artificial neural network (ANN) which may include a convolutional neural network (ANN e.g. CNN), that is trained may be recalled in block 226. The trained ANN may be trained with appropriate image data, such as a training set of image data of the same region or portion imaged in the accessed MR images in block 224. For example, the ANN may be trained with classified or identified regions, such as ROIs that may be within the access MR image. Various ROIs may include anatomical or feature regions or constructs that relate to beginning and ending regions of known or identified given fiber neural tracts. They may also include regions that the tract is known to pass or not pass through. Selected ROIs may include starting regions of the corticospinal tract in the brainstem (e.g. parts of the cerebral peduncle), ending regions of the corticospinal tract in the pre-central and post-central gyrus.

The trained ANN, therefore, that is trained on prior image data, may be stored with appropriate weights for various neurons in the ANN for identifying ROI's in new images. For example, the accessed MR images in block 224 may be of the subject 24. The trained ANN may be used, therefore, to identify ROI's in the accessed MR images from block 224 in block 230. The application or identification of ROI's in the MR images in block 230 may assist in identifying ROI's of beginning and ending regions of neuronal tracts. The identified ROI's may assist in identifying given or selected neuronal tracts to assist in segmenting neuronal tracts in the method 200. Output of segmented brain regions or ROI's may be made in block 240. The output segmented brain regions may include starting or ending ROI's, such as identified in a training image data for the CNN, or any appropriate brain regions. They may also include regions that the tract is known to pass or not pass through. Other appropriate brain regions may include selected anatomical or physiological brain regions such as the pre-central and post-central gyrus, cerebral peduncle, primary visual cortex, lateral *geniculate* nucleus.

As discussed above, in method 100, a classification system may be used to automatically identify, also referred to as classify, tracts (e.g. neuronal tracts) from diffusion weighted gradient images. Accordingly, the method 200 may also recall a trained classification system in block 120'. The recalled trained classification system may be similar to that discussed above in the recalled training classification system in block 120 in method 100, but it may have inputs from sub-process 220.

The sub-process 220 may also or alternatively be an input to the or with the recalled trained classification system in block 120'. Thus, the sub-process 220 may be used as an input with the process 200. The sub-process 220 allows the segmentation to include selected information or segmentation regarding ROIs.

The recalled trained classification system may be used to automatically identify or segment image tract in block 130. The automatic identification of the image tracts may be similar to that discussed above in block 130. As illustrated in the method 200, the sub-process 220 may also be a separate input for the automatic segmentation in block 130'. The output segmented regions in block 240, therefore, may also or alternatively be input to the automatic segmentation block 130'.

The segmentation of given neuronal tracts in block 130' may be performed automatically by execution of the trained classification system recalled in block 120'. The identification of or segmentation of selected regions in the image, such as a brain, from block 240 may assist or provide beginning and ending points of neuronal tracts, or other appropriate regions in the image. The other image regions may assist in the classification system in identifying and classifying the neural tracts. As discussed above, the neuronal tracts may be identified given various characteristics, and selected beginning and ending regions (or other regions that tract passes or does not pass through) may assist in identifying the neuronal tracts as the fiber tracts in the images. Nevertheless, the identification of selected regions in the image and segmentation thereof, may assist in the identification and segmentation of the given neuronal tracts in block 130'.

Thus, the method 200 may include various alternative or additional processes. For example, the method 200 may automatically segment in block 130' with the input from the sub-process 220 that identifies the ROIs in the image.

The segmented neuronal tracts may then be output in block 140', similar to the output in block 140, as discussed above. The process 200 may then end in block 150', also similar to the end in block 150 above. Accordingly, the output of the segmented neuronal tracts may include any appropriate output and the ending of the process 200 may include various additional or separate procedures, as discussed above. Nevertheless, the method 200, that again may be executed with the processor module 48, as discussed above, may include segmentation of selected image regions and the output thereof in block 240 from the sent process or input 220 to assist in identification, automatically, of neuronal tracts in the accessed diffusion weighted images from block 108'.

Turning reference to FIG. 5 and with continued reference to FIGS. 1 and 2, a method and process 300 for segmenting fiber tracts is discussed. The method 300 may include various portions or features that are similar to the portions and features discussed above in the methods 100 and 200. Like blocks will be identified with similar numerals augmented with a double prime (") and will not be discussed in detail here again. Accordingly, the method 300 may be used to segment, including identifying, given neuronal tracts.

Initially the method 300, similar to the method 100 and the method 200, discussed above, may be executed by an instruction in a selected algorithm or program by a selected processor, such as the processor module 48. Accordingly, it is understood that the method 300 may be performed by the workstation or processor system 40. The method 300 may be included in an algorithm that may be performed or carried out by a processor to assist and/or efficiently carry out a selected procedure, as discussed further herein.

Accordingly, the method 300 may begin in start block 304. Starting in block 304 may be similar to that as discussed above, such as in block 104. Accordingly various operations may be used to begin the process 300. After starting in block 304, a recall or accessing of diffusion weighted gradient image data may be made in block 108". After accessing the recalled diffusion weighted images a tractography of the image may be made in the block 112". The image tractography may be similar to the entire image tractography as discussed above in blocks 112 and 112'. The image tractography may then be output as an image (e.g. brain) tractography in block 116".

The process 300, however, may further include additional and/or alternative processes, including generating a noisy diffusion tractography based on the selected tractography from block 112". The noisy tractography may be generated with various additional inputs, as discussed herein. The noisy diffusion tractography, therefore, may include and/or be the result of a selected tractography algorithm that identifies the possible tracts due to the diffusion weight information collected in the image data accessed in block 108".

As also discussed above in the method 200, the selected sub-method or process 220" may be used to assist in identifying various ROI's in the image. The sub-process 220" may be similar to that as discussed above, and will be briefly recited here. Accordingly, MR images may be accessed or recalled in block 224". A recalled trained ANN may be made in block 226", as discussed above for block 226. The trained ANN may be similar to that discussed above in block 226 and, therefore, may be trained with selected images to identify various ROI's in an image.

The trained CNN may be applied to evaluate the accessed images in block 230". Thereafter, output segmented regions, such as selected ROI's including beginning and endings of selected fiber tracts, may be made in block 240". The output segmented ROI's may then be input to the noisy diffusion in 210" to assist in identifying selected regions for classification or identifying specific or given neuronal tracts in an image.

The method 300 may include recalling a trained machine learning system, such as one or more artificial neural networks (ANN) (e.g. a generative adversarial network) in block 320. The trained machine learning system may include an artificial neural network that is trained to segment tract for given neuronal tracts in an image tractography. The trained machine learning system may be trained in any appropriate manner, and include appropriate weights to adjust input to an activation function to provide an appropriate output. Generally, the weights may be applied to various inputs used to calculate an activation function. Upon the appropriate value, the activation function is activated to provide an output for assisting and determining a selected feature. The trained machine learning system may, therefore, be trained on selected inputs, such as inputs of identified tracts. The identified tracts may be identified by a selected user, such as a neurosurgeon, that identified tracts in a training data. The machine learning system may then be trained on the training data and then saved to be applied to additional input data, including the accessed images in the entire or image tractography, as discussed above. It is understood, however, that various machine learning systems may include semi- or un-supervised methods.

Accordingly, after recalling the trained machine learning system in block 320, automatic segmentation of the given fiber neuronal tracts may be made in block 330. The automatic segmentation in block 330 uses the trained machine learning system to identify the specific or given tracts in the image. The automatic segmentation in block 330 may, again, be performed by the processor module 48 that includes executing instructions of the recalled trained ML from block 320 and other selected inputs.

Also, the sub-process 220" may optionally provide an input with the trained machine learning system in block 320 for the automatic segmentation 330. In other words, the segmented ROI's output in block 240" may or may not be in put for the selected segmentation of the image tractography from block 116" automatic segmentation in block 330. Thus, the automatic segmentation may or may not be made with the assistance of the segmented ROI from the sub-process 220".

After the automatic segmentation in block 320, the automatically segmented fiber tracts for given neuronal tracts may be output in block 140". The output may be similar to that discussed above in blocks 140, 140'. Thereafter, the method 300 may end in block 150". Again, as discussed above, the ending of the process 300 in block 150" may lead to various additional procedures or processes, such as using the segmented neuronal tracts for a selected procedure, such as a resection of a tumor, implantation of a lead, or other appropriate procedure.

The various methods, including method 100, method 200, and method 300, as discussed above, include general features that may be included in an algorithm to segment fiber tracts in a selected image data set. As discussed above, the methods may include various features or processes that may be carried out by a selected system, such as the processor module 48, when performing the selected method. With reference to FIGS. 3-5, therefore, and with additional reference to FIG. 6A, an algorithm or method 500 is illustrated for assisting in training a system for automatic segmentation, as discussed above. The method 500 may be incorporated into the processes discussed above, including the methods 200, 300, and 400 to generate or allow for segmentation of given fiber tracts according to the selected methods, as discussed above. In various embodiments, one or more of the processes of the method 500 may be included in the methods 100, 200, 300 discussed above.

Generally, therefore, the method 500 may include accessing diffusion gradient images in block 510. The accessed gradient diffusion images in block 510 may be similar to those as discussed above. The accessed gradient diffusion images may then be processed to determine a tractography in the block 514 in the accessed image 510. The tractography processing in block 514, may also be similar to that as discussed above, including various tractography algorithms to identify tracts or possible tracts within the images accessed in block 510. Selected specific fibers may be identified in a tractography, according to the method 500, in line with the methods 200-400, as discussed above.

In the method 500, various processing may occur to the tractography processed image data may be output and/or accessed after or from the tractography processing in block 514. For example, a directionally encoded collar (DEC) fractional anisotropy (FA) map may be generated accessed in block 520. The DEC/FA image may include one that is identified based upon the accessed image data according to generally known techniques. In addition, a BO mask image in block 524 and a BO image in block 528 may be accessed and applied to the tractography processing. The BO mask and image may include images with no diffusion information included therein. Further, a selected image (e.g. brain) tractography, which may include a whole brain tractography (WBT) in block 532 may also output from the tractography processing.

The tractography outputs may be, optionally, registered to one or reference images in block 536. If registered, the registered image may also transformed with the DEC/FA. The registration to the reference space may include appropriate scaling and spatial transformation in block 536. The registration to the reference space may allow for a determination of a position or various feature of the identified image tractography.

A creation or determination of negative tracts may be made in block 540. Negative tracts are those fibers in the image tractography that are not part of the neuronal tracts that the system is trained to classify/segment. Positive tracts are those fibers belonging to the neuronal tracts that the system is trained to classify/segment, and they are created by a trained expert (e.g. a neuroradiologist). The creation of the negative tracts at 540 may be generated or created, such as by filtering tracts farthest in distance and most different in shape from the positive tracts. Various additional processing may occur, such as the negative tracts and positive tracts may also then be augmented in block 546. Augmentation may include random rotation, scaling, translation, and the addition of a Gaussian and other types of noise to the fiber and image features.

The tracts in the data, as discussed above, may then be analyzed and processed for training of selected segmentation methods of the given tracts. The segmentation training may occur according to various techniques, which may occur in tandem or separately. Thus, training may occur at least two paths, together or alternatively, to train selected systems.

In various embodiments, a classification system may be trained, thus, path 564 may be followed to compute various features of each line in block 560. The features can include various determinations or analyses of the various tracts, which may also be referred to as lines, for further segmentation and identification into fiber tracts as discussed above, and further herein. For example a number of points and location of points along the tract line may be determined. Vectors of each line segment between points may be determined, such as relative to each other and from each of the respective points. Fractional anisotropy (FA) values may be determined or calculated for each point. Also directionally encoded color information may be calculated or determined for each point. Curvature at each point, such as to each of the adjacent points, may also be calculated along each of the tracts. In various embodiments, an atlas may also be identified or accessed, such as a generally known brain atlas image or model and comparison to the structure of the identified tracts may be made. Appropriate brain atlases may include those included in the open-source application Freesurfer, or FSL (created by the FMRIB group in Oxford, UK). Further computations may include a length of a tract between a starting region or a point and/or an end region or point. Accordingly, an entire length of a tract may be measured or computed for each of the tracts in the image.

Input regarding a region of interest sub-process 580 may also be made. The region of interest sub-process 580 may be similar to the region of interest sub-process 220, as discussed above. Accordingly, accessing of anatomical image data in block 584 may be made and a recognition of various regions, such as starting and ending regions, anatomical features or structures, or the like may be made in block 588. The recognition of the various features may include the application of a machine learning system, such as that discussed above, including a CNN. The CNN may be trained with various data and the trained CNN may be used to identify structures or regions in accessed image data, such as the image data accessed in block 584. Nevertheless, the ROI sub-process 580 may be used to identify ROI to assist in a determination or segmentation of selected neuronal fibers. The input from the sub-process 580 may be included and/or augment the computed features in block 560.

The sub-process 580 may also access or compare to selected fiber tract atlases in block 592. Atlases may include models of fiber tracts that may be used to analyze or process tracts in the segmentation of block 514. Thus, the sub-processes 580 may utilize selected atlases of fiber tracts.

In the classification system training, a classification system for training may be recalled or generated in block 610. The training classification system may include appropriate classification systems, such as those discussed above including a random force or other appropriate classification system.

During training, or any selected time, the classification system may be used to classify and segment appropriate or given neuronal fibers in the accessed diffusion gradient image data in block 510. The segmentation may be performed automatically, as discussed above. The tractography may, therefore, be classified in block 620 with the recalled classification system. The classification may be similar to that as discussed above, based upon the trained classification systems.

After the classification or segmentation of the fiber tracts, the classified or segmented fiber tracts belonging to given neuronal tracts may be output in block 630. The output may be any appropriate output, including those discussed above. The output may include a display of the segmented neuronal tract, saving of the segmented neuronal tracts for additional analysis, or other appropriate outputs.

In various embodiments, a second or alternative path 634 may be followed. The path 634 directs to training a machine learning system for segmentation in block 636. The machine learning system may include an artificial neural network, such as a convolution neural network. The ML training in block 636 may be performed with the input for the tractography in block 514 and may include the optional reference image registration. In various additional or alternative embodiments, the training the ML may also include the computed features from block 560. Thus, the training the ML in block 636 may include selected inputs, as discussed above. The training of the ML may also, therefore, lead to segmentation of fiber tracts in block 620.

The method 500 may then output and/or save the trained system in block 634. In various embodiments, the output may be updated or validated such as increasing training data and/or outputs may be confirmed or checked for training progress. Thus, the trained systems may be saved or stored at a selected time and/or when the systems are appropriate trained in block 634.

The method 500 may end in block 640. The ending of the process 500 may be similar to the ending of the processes 200-400, as discussed above. Accordingly, the output from block 630 may be used to assist in identifying appropriate fiber tracts in a selected subject, such as the subject 24. The segmented fiber tracts may be used to assist in various procedures, such as a resection of a tumor, implantation of a device, or other appropriate procedures. Accordingly, the output 630 may be used to assist in performing a procedure and/or planning a procedure on a selected subject, such as a human subject for a selected procedure.

The method 500 may be a training process to train selected systems, such as a classification or machine learning system for segmentation of fiber tracts. The training system may then be used at a selected time to segment fiber tracts, such as according to methods as discussed above. Generally, with reference to FIG. 6B, a method 700 may be used to segment the data to segment fiber tracts.

The segmentation method 700, may be similar to the training method 500, and similar or identical blocks will use the same reference number augmented with a prime ('). The segmentation method 700, however, may include or utilize the trained systems to segment fiber tracts, as discussed above. Therefore, the method 700 may include accessing diffusion gradient images in block 510'. The accessed gradient diffusion images in block 510' may be similar to those as discussed above. The accessed gradient diffusion images may then be processed to determine a tractography in the block 514' in the accessed image 510'. The tractography processing in block 514', may also be similar to that as discussed above, including various tractography algorithms to identify tracts or possible tracts within the images accessed in block 510'. Selected specific fibers may be identified in a tractography, according to the method 700, in line with the methods 200-400, as discussed above.

In the method 700, various processing may occur to the tractography processed image data may be output and/or accessed after or from the tractography processing in block 514'. For example, a directionally encoded collar (DEC) fractional anisotropy (FA) map may be generated accessed in block 520'. The DEC/FA image may include one that is identified based upon the accessed image data according to generally known techniques. In addition, a B0 mask image in block 524' and a B0 image in block 528' may be accessed and applied to the tractography processing. The B0 mask and image may include images with no diffusion information included therein. Further, a selected image (e.g. brain)

tractography, which may include a whole brain tractography (WBT) in block 532' may also output from the tractography processing.

The tractography outputs may be, optionally, registered to one or reference images in block 536'. If registered, the registered image may also transformed with the DEC/FA. The registration to the reference space may include appropriate scaling and spatial transformation in block 536'. The registration to the reference space may allow for a determination of a position or various feature of the identified image tractography.

In various embodiments, a classification system may be used to segment the fiber tracts, thus, path 564' may be followed to compute various features of each line in block 560'. The features can include various determinations or analyses of the various tracts, which may also be referred to as lines, for further segmentation and identification into fiber tracts as discussed above, and further herein. For example a number of points and location of points along the tract line may be determined. Vectors of each line segment between points may be determined, such as relative to each other and from each of the respective points. Fractional anisotropy (FA) values may be determined or calculated for each point. Also directionally encoded color information may be calculated or determined for each point. Curvature at each point, such as to each of the adjacent points, may also be calculated along each of the tracts. In various embodiments, an atlas may also be identified or accessed, such as a generally known brain atlas image or model and comparison to the structure of the identified tracts may be made. Appropriate brain atlases may include those included in the open-source application Freesurfer, or FSL (created by the FMRIB group in Oxford, UK). Further computations may include a length of a tract between a starting region or a point and/or an end region or point. Accordingly, an entire length of a tract may be measured or computed for each of the tracts in the image.

Input regarding a region of interest sub-process 580' may also be made. The region of interest sub-process 580' may be similar to the region of interest sub-process 220, as discussed above. Accordingly, accessing of anatomical image data in block 584' may be made and a recognition of various regions, such as starting and ending regions, anatomical features or structures, or the like may be made in block 588'. The recognition of the various features may include the application of a machine learning system, such as that discussed above, including a CNN. The CNN may be trained with various data and the trained CNN may be used to identify structures or regions in accessed image data, such as the image data accessed in block 584'. Nevertheless, the ROI sub-process 580' may be used to identify ROI to assist in a determination or segmentation of selected neuronal fibers. The input from the sub-process 580' may be included and/or augment the computed features in block 560'.

The sub-process 580' may also access or compare to selected fiber tract atlases in block 592'. Atlases may include models of fiber tracts that may be used to analyze or process tracts in the segmentation of block 514'. Thus, the sub-processes 580' may utilize selected atlases of fiber tracts.

In the classification system, a trained classification system may be recalled in block 610'. The trained classification system may include appropriate classification systems, such as those discussed above including a random force or other appropriate classification system.

The trained classification system may be used to classify and segment appropriate or given neuronal fibers in the accessed diffusion gradient image data in block 510. The segmentation may be performed automatically, as discussed above. The tractography may, therefore, be classified in block 620' with the recalled classification system. The classification may be similar to that as discussed above, based upon the trained classification systems.

After the classification or segmentation of the fiber tracts, the classified or segmented fiber tracts belonging to given neuronal tracts may be output in block 630'. The output may be any appropriate output, including those discussed above. The output may include a display of the segmented neuronal tract, saving of the segmented neuronal tracts for additional analysis, or other appropriate outputs.

In various embodiments, a second or alternative path 634' may be followed. The path 634' directs to a trained machine learning system for segmentation in block 636'. The machine learning system may include an artificial neural network, such as a convolution neural network. The ML training in block 636' may be performed with the input for the tractography in block 514' and may include the optional reference image registration. In various additional or alternative embodiments, the training the ML may also include the computed features from block 560'. Thus, the training the ML in block 636' may include selected inputs, as discussed above. The training of the ML may also, therefore, lead to segmentation of fiber tracts in block 620'.

The method 700 may also provide output in block 630'. The output from block 630' may be used to assist in identifying appropriate fiber tracts in a selected subject, such as the subject 24. The segmented fiber tracts may be used to assist in various procedures, such as a resection of a tumor, implantation of a device, or other appropriate procedures. In various embodiments, an instrument may be navigated in the relative to the fiber tracts. Also, ablation planning and tracking may be performed. Accordingly, the output 630 may be used to assist in performing a procedure and/or planning a procedure on a selected subject, such as a human subject for a selected procedure. The process 700 may also then end in block 640', similar to the ending of the processes 200-400, as discussed above.

In light of the above, a selected system may automatically segment appropriate or given fiber tracts in an accessed diffusion gradient image data. In various embodiments, the data may be data relating to nerves or nerve bundles (e.g. brain data) and, therefore, the tracts may also be referred to as fiber neuronal tracts in a brain image. The automatic segmentation may be performed by a selected processor module to identify fiber tracts within a selected subject. The identifiable fiber tracts may include any appropriate fiber tracts such as optic radiations, an arcuate fasciculus (AF), a superior longitudinal fasciculus (SLF), a corticospinal tract (CST), frontal aslant tract (FAT), a fornix tract, a dentato rubro thalamic tract (DRT), or any other appropriate tracts. Nevertheless, the automatic segmentation may allow for minimal or no user intervention and identify relevant fiber tracts in a subject.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method to segment neuronal tracts in an image, comprising:
   accessing selected data of a subject;
   evaluating the accessed selected data to determine an image tractography including a plurality of tracts;
   evaluating at least a sub-plurality of tracts of the plurality of tracts with a trained machine learning algorithm;
   determining whether at least one of the evaluated sub-plurality of tracts is a given fiber neuronal tract based at least on the evaluation of at least the sub-plurality of tracts of the plurality of tracts;
   outputting which at least one tract of the plurality of tracts is/are the given fiber neuronal tract when at least one of the evaluated plurality of tracts is determined to be the given fiber neuronal tract; and
   wherein evaluating the accessed selected data to determine the image tractography including the plurality of tracts includes:
   determining an anisotropy of water within the selected data; and
   determining tracts through an image in the selected data based on the determined anisotropy.

2. The method of claim 1, wherein the accessed selected data includes diffusion weighted gradient images.

3. The method of claim 1, wherein the given fiber neuronal tract is at least one of a cortico-spinal tract, an optical tract, a frontal aslant tract, a dentato rubro thalamic tract, a fornix tract, or combinations thereof.

4. The method of claim 1, further comprising:
   training a machine learning algorithm to identify the given fiber neuronal tract to generate the trained machine learning algorithm with at least training data including the given fiber neuronal tract identified therein.

5. The method of claim 1, further comprising:
   navigating an instrument relative to the given fiber neuronal tract.

6. A method to segment neuronal tracts in an image, comprising:
   accessing selected data of a subject;
   evaluating the accessed selected data to determine an image tractography including a plurality of tracts;
   evaluating at least a sub-plurality of tracts of the plurality of tracts with a trained machine learning algorithm;
   determining whether at least one of the evaluated sub-plurality of tracts is a given fiber neuronal tract based at least on the evaluation of at least the sub-plurality of tracts of the plurality of tracts;
   outputting which at least one tract of the plurality of tracts is/are the given fiber neuronal tract when at least one of the evaluated plurality of tracts is determined to be the given fiber neuronal tract; and
   wherein evaluating the sub-plurality of tracts includes at least one of:
   determining points along each tract of the sub-plurality of tracts;
   evaluating a fractional anisotropy at each point of the determined points;
   evaluating a diffusion-encoded-color at each point of the determined points;
   determine a distance from a starting region of each tract to an ending region of each tract; and
   determine a curvature of the tract at each point of the determined points.

7. A method to segment neuronal tracts in an image, comprising:
   accessing selected data of a subject;
   evaluating the accessed selected data to determine an image tractography including a plurality of tracts;
   evaluating at least a sub-plurality of tracts of the plurality of tracts with a trained machine learning algorithm;
   determining whether at least one of the evaluated sub-plurality of tracts is a given fiber neuronal tract based at least on the evaluation of at least the sub-plurality of tracts of the plurality of tracts;
   outputting which at least one tract of the plurality of tracts is/are the given fiber neuronal tract when at least one of the evaluated plurality of tracts is determined to be the given fiber neuronal tract; and
   determining selected regions of interest relative to the accessed selected data with a recalled trained convolutional neural network.

8. The method of claim 7, further comprising:
wherein evaluating the accessed selected data to determine an image tractography includes evaluating an entire image to determine a plurality of tracts.

9. The method of claim 8, further comprising:
recalling the trained convolutional neural network;
accessing anatomical image data of the subject; and
determining at least one region of interest in the accessed image data with the recalled trained convolutional neural network.

10. The method of claim 9, wherein determining the selected regions of interest relative to the accessed selected data with the recalled trained convolutional neural network includes identifying the determined at least one region of interest determined in the accessed image data in the accessed selected data of the subject.

11. The method of claim 10, wherein the at least one region of interest includes at least one of a starting region of the given fiber neuronal tract or an ending region of the given fiber neuronal tract.

12. The method of claim 10, further comprising:
determining at least one tract of at least the sub-plurality of tracts that interacts with the determined at least one region of interest;
wherein evaluating at least the sub-plurality of tracts of the plurality of tracts includes evaluating only the determined at least one tract.

13. The method of claim 7, further comprising:
recalling the trained convolutional neural network;
accessing anatomical image data of the subject; and
determining at least one region of interest in the accessed image data with the recalled trained convolutional neural network.

14. The method of claim 13, wherein determining the selected regions of interest relative to the accessed selected data with the recalled trained convolutional neural network includes identifying the determined at least one region of interest determined in the accessed image data in the accessed selected data of the subject.

15. The method of claim 14, wherein evaluating at least the sub-plurality of tracts of the plurality of tracts with the recalled trained classification system includes evaluating the sub-plurality of tracts based on the determined at least one region of interest determined in the accessed image data.

16. A system configured to segment given neuronal tracts in an image of a subject, comprising:
a processor system configured to execute instructions to:
  access a selected data of a subject;
  evaluate the accessed selected data based on a first criteria to determine an image tractography including a plurality of tracts;
  evaluate at least a sub-plurality of tracts of the plurality of tracts with a trained machine learning algorithm;
  determine whether at least one of the evaluated sub-plurality of tracts is a given fiber neuronal tract based at least on the evaluation of at least the sub-plurality of tracts of the plurality of tracts; and output which at least one tract of the plurality of tracts is/are the given fiber neuronal tract when at least one of the evaluated plurality of tracts is determined to be the given fiber neuronal tract;
wherein the processor system is configured to execute further instructions to determine selected regions of interest relative to the accessed selected data with a recalled trained convolutional neural network;
wherein the determination of whether at least one of the evaluated sub-plurality of tracts is a given fiber neuronal tract is further based on the determination of selected regions of interest.

17. The system of claim 16, further comprising:
a memory system configured to store the instructions.

18. The system of claim 16, further comprising:
a display device configured to display an image of the subject and the outputted given fiber neuronal tract.

19. The system of claim 16, further comprising:
an imaging system configured to acquire diffusion weighted gradient images of the subject.

20. The system of claim 16, further comprising:
a navigation system including a tracking system and a tracking device;
wherein an instrument is operable to be navigated relative to the output given neuronal tract within the navigation system.

* * * * *

UNITED STATES PATENT AND TRADEMARK OFFICE
CERTIFICATE OF CORRECTION

PATENT NO. : 11,508,070 B2
APPLICATION NO. : 16/862890
DATED : November 22, 2022
INVENTOR(S) : Rowena Vigh et al.

It is certified that error appears in the above-identified patent and that said Letters Patent is hereby corrected as shown below:

On the Title Page

In the illustrative figure, 6A, Ref. Numeral 584, Line 1, delete "AccessAnatomical" and insert --Access Anatomical--

In the Drawings

Figure 6A:
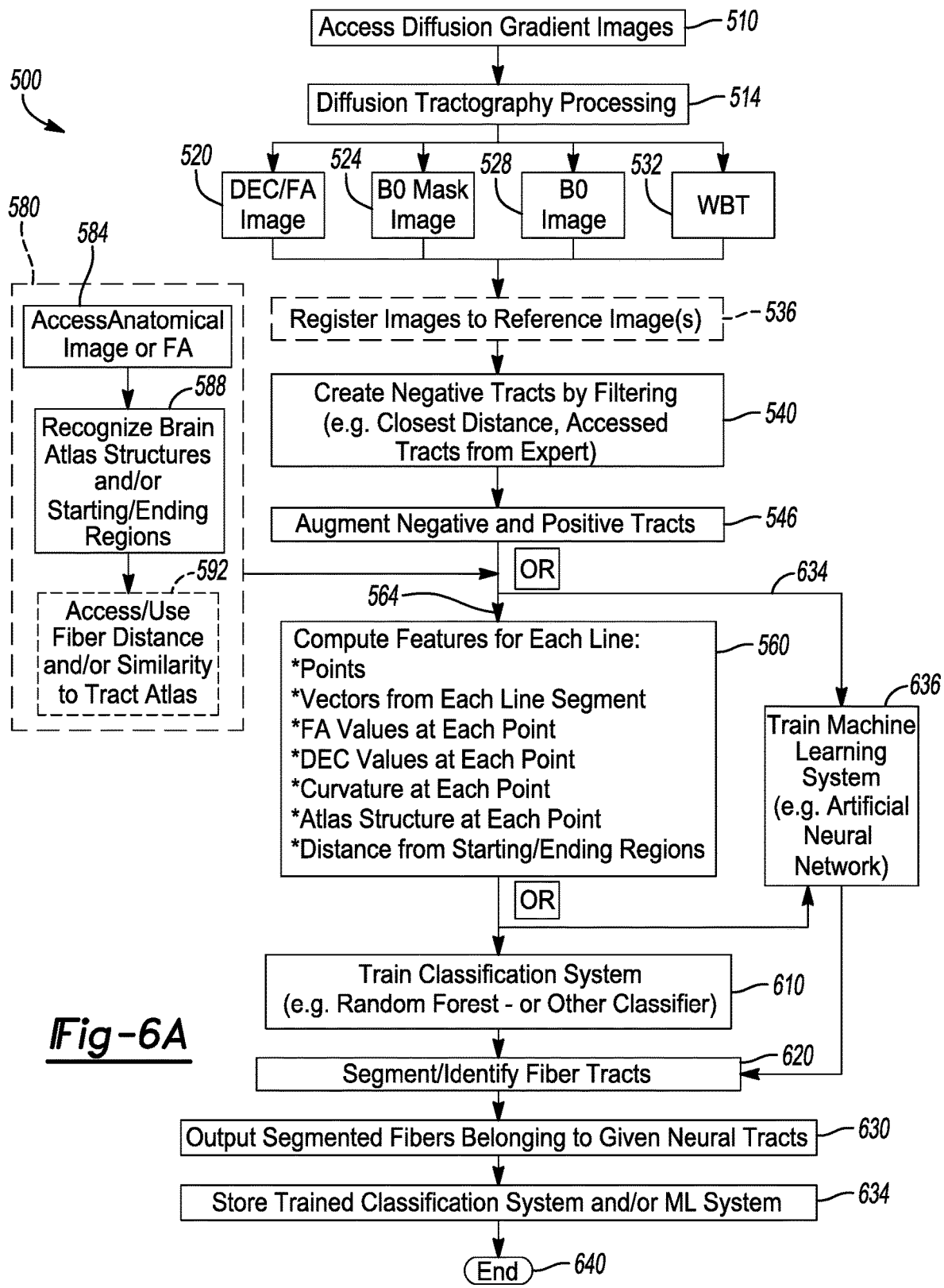
FIG. 6A is a flow chart of a method to train a system to segment image data, according to various embodiments.
Figure 6B:
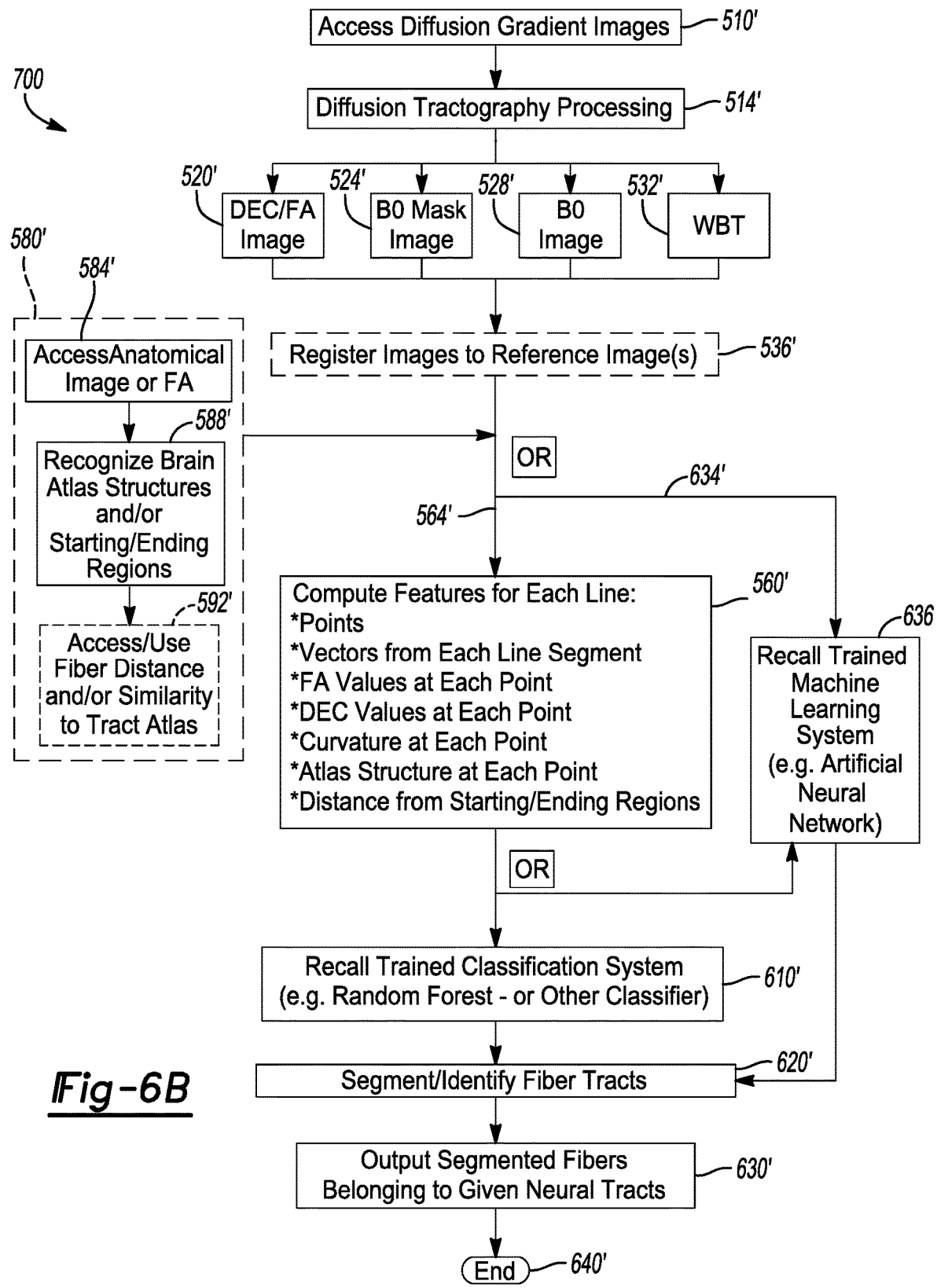
FIG. 6B is a flow chart of a method to use a system to segment image data, according to various embodiments.

Sheet 6 of 7, Fig. 6A, Reference Numeral 584, Line 1, Delete "AccessAnatomical" and insert --Access Anatomical-- therefor Sheet 7 of 7, Fig. 6B, Reference Numeral 584', Line 1, Delete "AccessAnatomical" and insert --Access Anatomical-- therefor In the Specification Column 1, Cross-Reference to Related Applications, Line 11, Delete "Applications" and insert --applications-- therefor Column 2, Detailed Description, Line 67, Delete "24" and insert --20-- therefor Column 3, Detailed Description, Line 30, Delete "52," and insert --58,-- therefor Column 3, Detailed Description, Line 66, Delete "74." and insert --24.-- therefor Column 7, Detailed Description, Line 6, Delete "78," and insert --58,-- therefor Column 7, Detailed Description, Line 8, Delete "bock" and insert --block-- therefor Column 7, Detailed Description, Line 18, Delete "78," and insert --58,-- therefor Signed and Sealed this
Eighth Day of August, 2023

Katherine Kelly Vidal
*Director of the United States Patent and Trademark Office*

CERTIFICATE OF CORRECTION (continued)
U.S. Pat. No. 11,508,070 B2

Column 7, Detailed Description, Line 26, Delete "78" and insert --58-- therefor

Column 7, Detailed Description, Line 34, Delete "78" and insert --58-- therefor

Column 7, Detailed Description, Line 36, Delete "78" and insert --58-- therefor

Column 8, Detailed Description, Line 5, Delete "C)" and insert --(')-- therefor

Column 12, Detailed Description, Line 29, Delete "BO" and insert --B0-- therefor Column 12, Detailed Description, Line 30, Delete "BO" and insert --B0-- therefor Column 12, Detailed Description, Line 31, Delete "BO" and insert --B0-- therefor Column 14, Detailed Description, Line 63, Delete "BO" and insert --B0-- therefor Column 14, Detailed Description, Line 64, Delete "BO" and insert --B0-- therefor Column 14, Detailed Description, Line 65, Delete "BO" and insert --B0-- therefor In the Claims Column 20, Line 15, In Claim 16, after "and", insert --¶--